United States Patent
Behdjati et al.

(10) Patent No.: US 7,533,305 B2
(45) Date of Patent: May 12, 2009

(54) METHOD AND APPARATUS FOR STRUCTURED DETECTION AND HANDLING OF PROBLEMS OCCURRING IN A COMPUTERIZED SYSTEM

(75) Inventors: Aresu Behdjati, München (DE); Klaus Fronczek, Eckental (DE); Wolfgang Trautner, Hessdorf (DE)

(73) Assignee: Siemens Aktiengesellschaft, Munich (DE)

( * ) Notice: Subject to any disclaimer, the term of this patent is extended or adjusted under 35 U.S.C. 154(b) by 387 days.

(21) Appl. No.: 11/402,987

(22) Filed: Apr. 11, 2006

(65) Prior Publication Data

US 2007/0011124 A1     Jan. 11, 2007

(30) Foreign Application Priority Data

Apr. 11, 2005   (DE) ................. 10 2005 016 561

(51) Int. Cl.
*G06F 11/00* (2006.01)
(52) U.S. Cl. .................. 714/57; 714/46; 714/48
(58) Field of Classification Search .......... 714/57
See application file for complete search history.

(56) References Cited

U.S. PATENT DOCUMENTS

| | | | | |
|---|---|---|---|---|
| 6,029,258 A | * | 2/2000 | Ahmad ................. | 714/46 |
| 6,772,374 B2 | * | 8/2004 | Forman et al. ........ | 714/46 |
| 6,829,734 B1 | * | 12/2004 | Kreulen et al. ........ | 714/46 |
| 7,013,410 B2 | * | 3/2006 | Asauchi ................ | 714/46 |
| 7,325,170 B2 | * | 1/2008 | Srinivasan et al. .... | 714/46 |
| 2004/0153821 A1 | | 8/2004 | Kuhmann et al. | |
| 2004/0199828 A1 | | 10/2004 | Cabezas et al. | |
| 2005/0049996 A1 | | 3/2005 | Srinivasan et al. | |

* cited by examiner

*Primary Examiner*—Christopher S McCarthy
(74) *Attorney, Agent, or Firm*—Schiff Hardin LLP

(57) ABSTRACT

In a method and apparatus for structured detection and handling of problems occurring in a computerized system, data storage contains multiple data sets, each data set concerning a known problem that can occur in the system and each data set containing at least one solution approach to solve the problem in addition to a designation of the problem. A control device connected with the data storage for outputs data to a user interface at which a user sees the designation of the respective problems of the data sets stored in the data storage, and thus a selection by the user of a data set stored in the data storage is enabled. The control device outputs at least one solution approach to the user via the user interface dependent on the data set selected by the user. The user interface enables a simultaneous selection of a number of the data sets by the user, and the control device automatically determines at least one suitable solution approach dependent on the combination of the data sets selected by the user, and outputs the at least one suitable solution approach to the user via the user interface.

19 Claims, 4 Drawing Sheets

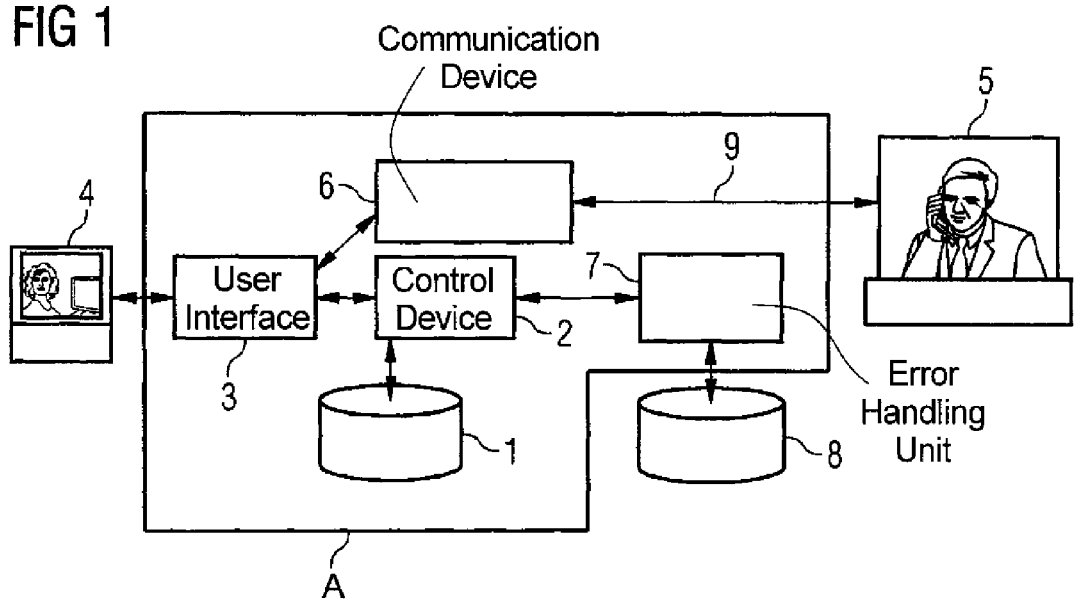

| | Designation 1 | Designation 2 | Designation 3 | Designation 4 | Designation 5 |
|---|---|---|---|---|---|
| Designation 1 | Solution 1 | Solution 12 | Solution 13 | Solution 14 | Solution 15 |
| Designation 2 | Solution 12 | Solution 2 | Solution 23 | Solution 24 | Solution 25 |
| Designation 3 | Solution 13 | Solution 23 | Solution 3 | Solution 34 | Solution 35 |
| Designation 4 | Solution 14 | Solution 24 | Solution 34 | Solution 4 | Solution 45 |
| Designation 5 | Solution 15 | Solution 25 | Solution 35 | Solution 45 | Solution 5 |

FIG 2

| Ref | Field | Value |
|---|---|---|
| 20 | Designation | Online storage overflow |
| 21 | Main category | Storage |
| 22 | Sub-category | Online storage |
| 23 | Synonym 1 | Access to I/O interface 32 is not possible |
| 23* | Synonym 2 | Storage capacity of online storage exceeded |
| 24 | Description | The system brings up the error message "Access to I/O interface 32 is not possible". Further data cannot be acquired; An access to already-acquired data is, however, still possible |
| 25 | Associated pattern in error file/check file | Paragraph 123 of the error file Segments 4456 through 9998 of the check file |
| 26 | Possibly connected problem | Lacking access authorization; Storage access |
| 27 | Solution approach 1 | Insert new storage medium; check robotics |
| 27* | Solution approach 1 | Specialist of the field of expertise 23 at +49/(0)89/12345 or mailto:23@spezialisten.de kontaktieren |
| 28 | Authorization | Authorized by Mr. Maier (Supervisor, area of expertise 23) |
| 29 | User association | Relevant for users of the areas of expertise 12, 15, 18, 19, 23, 40 |

30

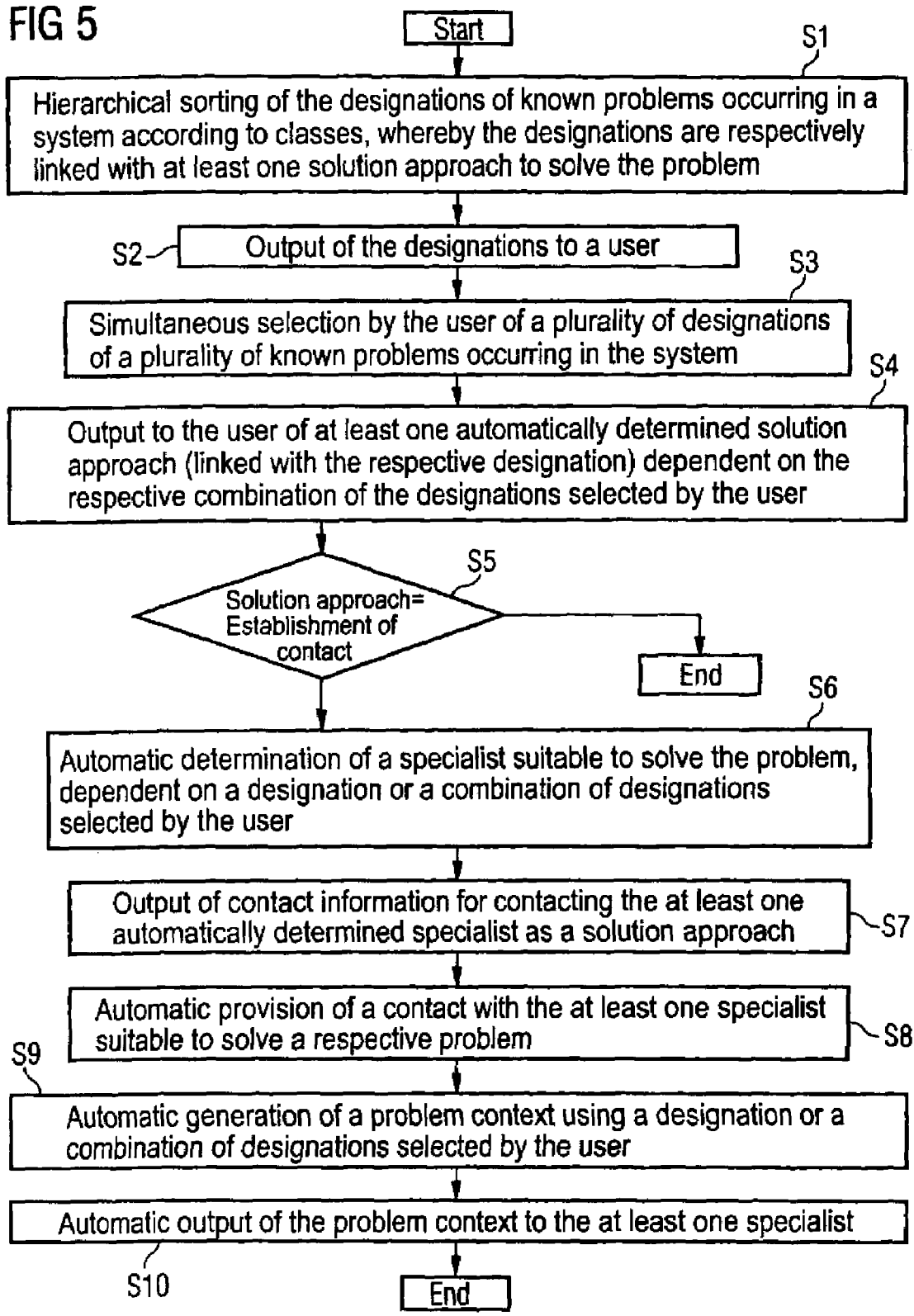

METHOD AND APPARATUS FOR STRUCTURED DETECTION AND HANDLING OF PROBLEMS OCCURRING IN A COMPUTERIZED SYSTEM

BACKGROUND OF THE INVENTION

1. Field of the Invention

The present invention concerns an apparatus for structured detection and handling of problems that occur in a computerized system.

2. Description of the Prior Art

Apparatuses and methods of the above general type have been known in the field of computer technology for a fairly long time. Numerous computer programs thus possess a "help" function. Given activation of the "help" function, a context menu is frequently opened which for the most part contains a content index structured in a hierarchical form as well as a search function for searching for individual search terms. After selection of a search term, instructions and explanations regarding the selected search term and, if applicable, solution suggestions are submitted to the user insofar as the selected search term concerns a known problem occurring in the system. A branching to other related search terms is frequently also possible.

Such "help" functions are for the most part not implemented in other fields of technology (such as, for example, medical technology) in which frequently no standard operating systems are used. A user of such systems is therefore normally forced to resort by telephone to a service center in order to obtain advice from a specialist to remedy the problem.

For the user this presents the difficulty of describing the problem in words, since the user normally does not know and/or understand the technical design of the respective system. Many problems are therefore frequently incomprehensible for a user. Furthermore, medical apparatuses are sold in many countries, such that the problem additionally occurs that a user cannot always use his or her native language on the hotline, but rather must use a different language (for example English). Experientially, the verbalization of a problem in a different language than the native language is very difficult for the user.

This has the consequence that the understanding between user and specialist is frequently unsatisfactory and requires a number of further inquiries. Even the appearance of the specialist on site is frequently necessary in order to obtain all information necessary for the correction of the problem. Furthermore, there is the problem that, upon calling the hotline, a user often initially does not know which specialists is needed for correction of the problem. As a consequence the user must often laboriously and reluctantly proceed through a number of false starts until the user finds the competent specialists for the correction of the problem, since the personnel used for service centers normally possess a very broad but not very deep expertise.

The help function described in the preceding and implemented in many computer programs also has the disadvantage that it is for the most part insufficient to handle complex problems, since dependencies and interactions among individual problems normally cannot be detected and remedied.

SUMMARY OF THE INVENTION

An object of the present invention is to provide an apparatus and a method for structured detection and handling of problems occurring in a system that enable the handling and remedy even of more complex problems in a simple manner with an optimally small personnel expenditure, and thus in an optimally cost-effective manner.

According to the present invention, an apparatus for structured detection and handling of problems occurring in a system has: a data storage in which is stored a plurality of data sets, whereby each data set concerns a known problem occurring in the system and each data set contains at least one solution approach to solve the problem in addition to a designation of the problem. A control device, connected to the data storage outputs data to a user interface, and the user interface, controlled by the control device, outputs the respective designations of a respective problem of the data set stored in the data storage to a user, and thus enables a selection by the user of a data set stored in the data storage. Dependent on the data set selected by the user, the control device outputs at least one solution approach to the user via the user interface. The user interface of the inventive apparatus enables a simultaneous selection of a number of data sets by the user, and, dependent on the respective combination of the data sets selected by the user, the control device automatically determines at least one suitable solution approach and outputs it to the user via the user interface.

Because the user interface of the inventive apparatus enables a simultaneous selection of a number of data sets by the user, even complex problems occurring in a system can be detected simply and with high precision. An optimal solution approach to remedy the problem is made available to a user even given complex problems, by the control device of the inventive apparatus automatically determining at least one suitable solution approach dependent on the combination of the data sets selected by the user, and thus dependent on the combination of interactions of various occurring problems, and outputs said at least one suitable solution approach to the user.

The user interface, controlled by the control device, outputs the respective designations of the data sets stored in the data storage to a user and thus provides a terminology databank, so verbalization of the problems is made easier since the provided terms must only be selected by a user and do not have to be laboriously created or found by the user. By the standardization of the designations of problems, the fear of the unknown that frequently occurs for users given the search for solution approaches for existing problems is reduced since linguistic problems of the user play a subordinate role.

Furthermore, by the automatic output of solution approaches by the control device via the user interface, it is ensured that problems that can be remedied by a user himself or herself can be solved without consultation with a specialist.

In a preferred embodiment, dependent on a data set or a combination of data sets selected by a user via the user interface, the control device automatically determines, as a solution approach, at least one specialist suitable for solving the problem, and via the user interface the control device automatically outputs contact information for contacting the specialist.

The automatic determination of a specialist suitable to solve a problem using the data set or combination of data sets selected by a user via the user interface, together with the automatic output of contact information for contacting of the specialist, ensures that a user is automatically, immediately referred to the specialists suitable for the correction of the problem. A repeated further relaying or forwarding of the user to various specialists unfamiliar with the subject is thus prevented. The inventive apparatus thus insures a particularly user-friendly support of the user.

It is advantageous for the apparatus to also include a communication device in order to automatically provide a contact with the specialist suitable to solve a particular problem.

By the automatic provision of a contact with the (at least one) specialist suitable to solve a particular problem, it is prevented by the inventive apparatus that a user inadvertently turns to a specialist not competent for the remedy of the problem.

In this case, using the at least one data set selected by the user the control device advantageously, automatically creates a problem context and outputs this via the communication device to the specialist.

By the automatic creation and output of a problem context to the specialist, the inventive apparatus ensures that a contacted specialist from the outset possesses all current information regarding the problem occurring in the system to be remedied. Since this information is automatically generated, it is standardized and easily intelligible for the specialist. Misunderstandings are thus reduced since the transferred information is uniformly understood. Furthermore, the transmission of unnecessary information to the specialist is prevented.

According to a further embodiment of the present invention, the apparatus also performs error handling by automatically searching through error files and/or check files created by the system for specific patterns and stores automatic links to these patterns in at least one data set of at least one associated problem.

For this purpose, in the error handling an error pattern databank stored that associates typical patterns in the error files and/or check files created by the system with specific problems. By means of the error handling of the inventive apparatus, it is ensured that even information that is unintelligible for a user, or not immediately accessible, can be taken into account in the detection and the correction of problems.

The user interface preferably outputs the designations of the data sets to the user hierarchically sorted according to categories.

Designations of data sets hierarchically sorted according to categories are particularly clear for a user and thus particularly easily understandable. Such an output furthermore compels the user to a structured process in the detection and handling of problems occurring in a system, so the problems can be detected and described more quickly since the user can be guided to the problem in steps.

In general, it is helpful when the data sets stored in the data storage are associated with various categories with associated sub-categories, with additional information about superordinate and/or subordinate categories being contained in the respective data sets. This enables a hierarchical structuring of the data sets in a particularly simple manner.

At least one synonym for the designation and/or additionally one description of the problem and/or additionally one notification of problems possibly connected with the respective problem preferably are stored in at least one data set.

The additional consideration of synonyms for the designation of the problem, and of the respective data set, enables even users with a relatively small vocabulary or users with different technical background knowledge to experience a comfortable operation with the inventive apparatus.

In order to be able to take into account an adaptation of the inventive apparatus to new realizations with regard to problems occurring in the system and remedy thereof, it is advantageous when the user interface enables an addition of: synonyms for the designation of the respective problem; and/or solution approaches; and/or information about superordinate and/or subordinate categories; and/or descriptions of the respective problem; and/or indications of problems possibly connected with the respective problem; to the data sets by the user and/or specialist.

In order to prevent the inventive apparatus from containing incorrect specifications regarding problems occurring in the system and possibilities regarding the remedy of these problems, an alteration of a data set by a user advantageously requires an authorization by a specialist.

The inventive method for structured detection and handling of problems occurring in a system includes the following steps:

output to the user of designations of known problems occurring in the system, whereby the designations are respectively linked with at least one solution approach to solve the problem;

selection by the user of a designation of a known problem occurring in the system;

output to the user of at least one solution approach linked with the respective designation, dependent on the designation selected by the user; and the selection by the user of a designation of a known problem occurring in the system encompasses the simultaneous selection of a number of designations of a number of known problems occurring in the system; and the step of output to the user of the at least one solution approach linked with the respective designation encompasses the output of at least one suitable solution approach automatically determined dependent on the respective combination of the designations selected by the user.

It is advantageous for the step of the output to the user of the at least one solution approach linked with the respective designation encompass:

an automatic determination of a specialist suited to solve the problem, dependent on a designation or a combination of designations selected by the user; as well as an output of contact information for contacting the at least one automatically-determined specialist as a solution approach.

The method also includes the following step:

automatic provision of a contact with the at least one specialist suited to solve a respective problem.

In this case it is particularly useful when the method also includes the following step:

automatic generation of a problem context using a designation or a combination of designations selected by the user; and automatic output of the problem context to the at least one specialist.

According to a preferred embodiment, the inventive method also includes the following steps:

automatic searching for specific patterns in error files and/or check files created by the system; and automatic linking of found patterns with at least one designation of at least one associated problem.

Furthermore it is advantageous for the step of the output to a user of designations of known problems occurring in the system includes a hierarchical sorting of the designations according to categories before the output to the user.

The method also preferably includes the following step:

addition of: synonyms for the designation of the problem; and/or solution approaches; and/or information about superordinate and/or subordinate categories; and/or descriptions of the problem; and/or indications of problems possibly connected with the problem; to the designations of known problems occurring in the system.

The above object is furthermore achieved by a computer program product having program code stored on a machine-readable medium, the computer program product being suitable for execution of the method as described above when loaded into the working memory of a computer.

DESCRIPTION OF THE DRAWINGS

FIG. 1 is a block diagram of the inventive apparatus for structured detection and handling of problems occurring in a system according to a preferred embodiment of the present invention.

FIG. 2 schematically shows the design of a data set used in the apparatus from FIG. 1.

FIG. 4 schematically illustrates the determination of suitable solution approaches, dependent on a combination of data sets selected by a user.

FIG. 5 is a block diagram of a preferred embodiment the inventive method for structured detection and handling of problems occurring in a system.

DESCRIPTION OF THE PREFERRED EMBODIMENTS

Figure 3A:
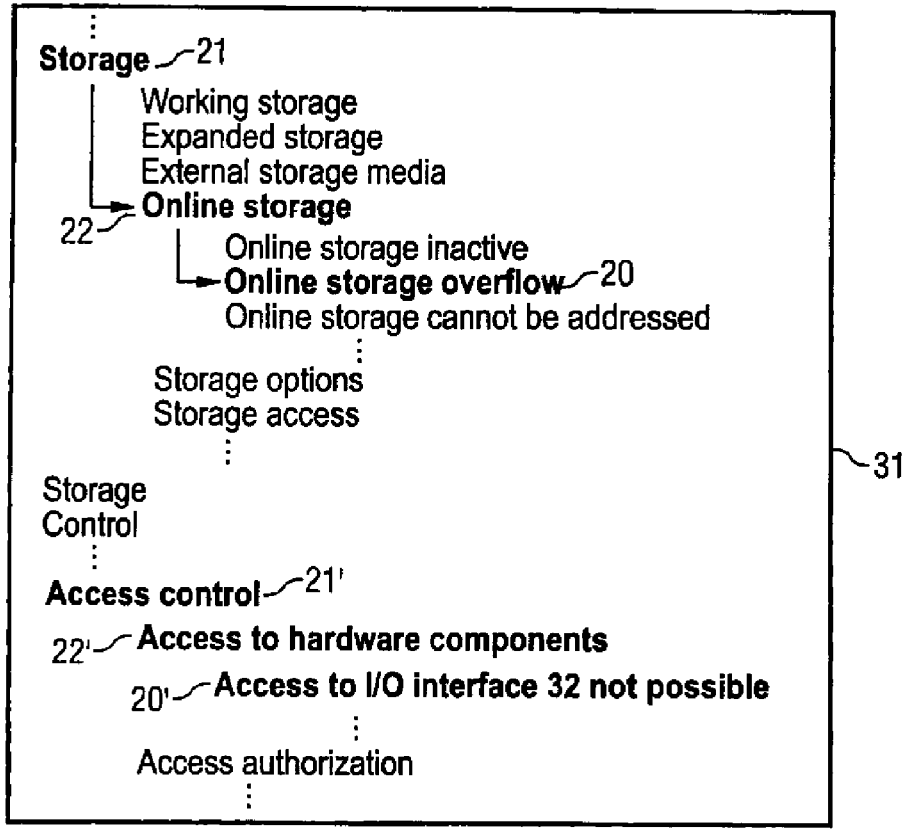
FIG. 3a schematically shows a first display of a user interface of the apparatus shown in FIG. 1.

In the preferred embodiment shown in FIG. 1, the inventive apparatus A for structured detection and handling of problems occurring in a system comprises a data storage 1, a control device 2 connected with the data storage 1, a user interface 3 connected with the control device, a communication device 6 connected with the user interface 3 as well as an error handling unit 7 connected with the control device 2.

The control device 2 connected with the data storage 1 outputs data read out from the data storage 1 to a user 4 of the apparatus 0 via the user interface 3. The output by means of the user interface 3 can ensue in a graphical manner in the form of a indicator or a printout. Alternatively an acoustic output is also possible.

The acoustic output can ensue by means of a speech generator, with speech input by the user being also provided. In the framework of this speech output, a selection of possibilities is also presented to the user from which the user can select (for example via speech input) in order to always further delimit the problem.

A number of data sets 30 is stored in the data storage 1. This data set 30 represents a known problem occurring in a system (for example a medical apparatus). In the present exemplary embodiment, it concerns a hard drive in the data storage 1.

As can be seen from FIG. 2, each data set 30 according to the preferred embodiment shown therein has a designation 20, an indication of the main category 21 associated therewith (and thus an indication of a superordinate category), an indication of an associated sub-category 22 (and thus an indication of a secondary superordinate category), two synonyms 23 and 23* for the designation 20 of the problem, a short description 24 of the problem occurring in the system, a reference pointer 25 to associated patterns in error files or check files of the system, a reference 26 to possibly connected problems, as well as at least one solution approach 27, 27* for solution of the problem. According to this preferred embodiment, each data set 30 furthermore has an authorization 28 and a user association 29. The authorization 28 specifies a user authorized to use the data set 30. The user association 29 specifies for which user a data set 30 is relevant.

The reference 25 to associated patterns in error files or check files of the system in the preferred exemplary embodiment shown here is automatically created by the error handling unit 7 connected with the control device 2. For this, the error handling unit 7 automatically searches through error files and/or check files created by the system (which error files and/or check files are typically stored on a fixed disk or a solid-state storage of the system) for specific patterns or error messages characteristic of problems and automatically stores a reference to these patterns in the respective data set 30 associated with the problem. For this purpose, an error pattern databank is advantageously stored in the error handling, which error pattern databank associates typical patterns in the error files and/or check files created by the system with specific problems. The reference can exist, for example, in the specification of the storage location of the respective pattern or even also in the reproduction of the pattern itself.

The automatic search for specific patterns by the error handling unit 7 unburdens a user 4 of the inventive apparatus 0 of the input of detailed knowledge and provides for more intelligence of the control device 2, and therewith for a better pre-analysis of the problem to be remedied, and thus for a better selection of the solution approach 27, 27* suitable for remedy of the problem, dependent on the respective combination of the data sets 30 selected by the user 4.

Controlled by the control device 2, the user interface 3 outputs the designations 20 of the data sets 30 (hierarchically sorted according to categories) to a user of the inventive apparatus 0 for structured detection and handling of problems occurring in a system. An example for such a hierarchical display 31 sorted according to categories is shown in FIG. 3A.

Only such data sets 30 that are relevant for a respective user due to the user association 29 contained therein are thereby advantageously used. A pre-selection thus advantageously occurs. This is particularly reasonable when a number of users of various technical fields access a common databank which contains the data sets 30.

As can be seen from FIG. 3A, the data sets 30 stored in the data storage 1 are associated with various main categories 21 with associated sub-categories 22. The corresponding information about superordinate and/or subordinate categories 21 and 22 are thereby contained in the respective data sets 30. Using this output (hierarchically sorted according to categories) via the user interface 3, the user can hierarchically navigate through the offered designations 20 of the data sets 30 and therewith locate the data sets 30 concerning the problem occupying the user 4.

A user is thus successively guided towards a solution by the user interface 3. Dependent on a user input, the user interface automatically selects the data sets that are relevant for a particular problem. The problem is thus always further delimited via the interplay between user interface 3 and user until a solution for the problem can be output to the user. This ensues via the output of a corresponding data set.

Dependent on a data set 30 selected by the user, according to a corresponding pre-selection the control device 2 outputs the data set 30 concerning information and in particular at least one respective solution approach 27, 27*.

Figure 3B:
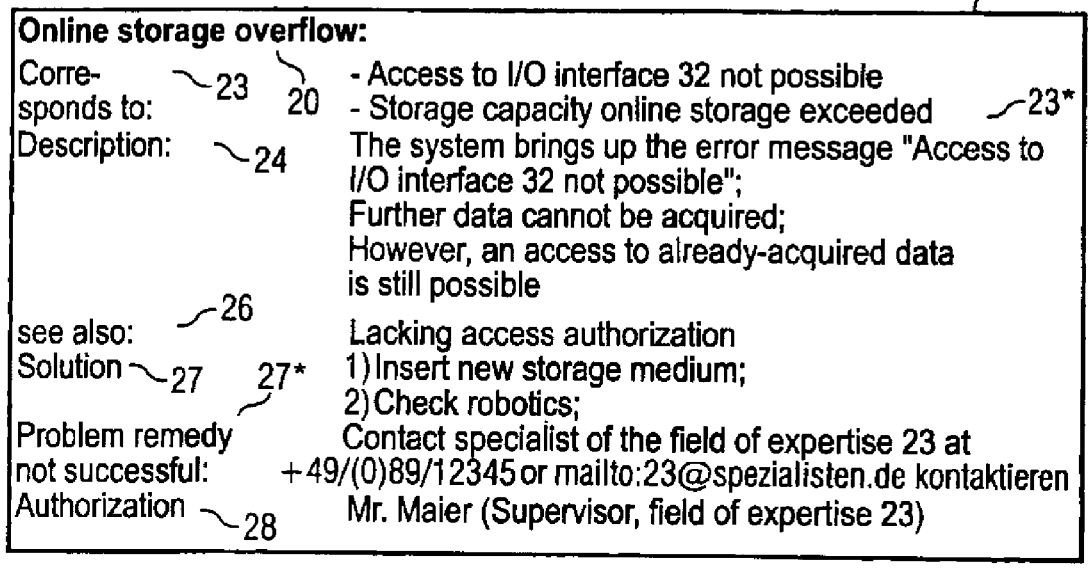
FIG. 3b schematically shows a second display of the user interface of the apparatus shown in FIG. 1.

An example of such a display 32 is shown in FIG. 3B. From FIG. 3B it can be seen that the data set 30 with which the designation 20 "Online storage overflow" is associated can alternatively also be designated as "Access to I/O interface 32 is not possible" or "Storage capacity online storage exceeded".

The same data set in the display 31 shown in FIG. 3A could correspondingly also be selected via selection of the designation 20' "Access to I/O interface 32 is not possible" of the super-category 22' "Access to hardware components" of the main category 21' "Access control".

The inventive apparatus supports the verbalization of problems by a user 4 via the use of the synonyms 23, 23*. The designations 20 of the problems occurring in the system thus do not have to be created by the user, but rather can be selected.

Since, in the preferred embodiment, each data set 30 also has a reference 26 to related problems and this reference (as shown in the display 32 of FIG. 3B) is also output to the User, in the inventive apparatus alternatives are automatically offered to the user in the event that a data set 30 does not entirely concern the problem considered by the user 4.

According to the present invention, the user interface 3 enables a simultaneous selection of a number of data sets 30 by the user, and therewith a linking of a number of designations 20 concerning a problem occurring in the system. Dependent on the respective combination of the data sets 30 selected by the user 4, the control device 2 automatically determines at least one suitable solution approach 27, 27* and outputs this to the user 4 via the user interface 3.

The determination of a suitable solution approach 27, 27* dependent on a respective combination of the data sets 30 selected by the user 4 is schematically shown in FIG. 4.

As shown in FIG. 4, in this example the designation "3" and the designation "4" were selected by the user 4 for description of the problem occurring in the system. As shown in FIG. 4, the solution "34" results for a combination of the designation "3" and the designation "4". Even when only suitable solution approaches for combinations of two designations 20 can be determined with the table shown in FIG. 4, it is clear to those skilled in the art that such a tabular procedure is also possible in more than two dimensions, and therewith also given the simultaneous selection of more than two designations 20. To determine the solution approaches suitable for combinations of designations 20, corresponding tables and/or functions can be stored in the data storage 1.

Even complex problems can be delimited and reliably handled by means of the inventive apparatus by the consideration of respective combinations of the data sets 30 selected by the user 4.

If no remedy of the problem is possible even by means of the solution approach 27 determined by the control device 2 (dependent on the respective combination of the data sets 30 selected by the user 4) and output via the user interface 3, in the preferred exemplary embodiment shown in FIG. 1, the control device 2 automatically (dependent on the data set 30 or a combination of data sets 30 selected by the user 4 via the user interface 3) determines at least one specialist 5 suitable to solve the problem as a solution approach 27* and automatically outputs contact information via the user interface 3 for contacting this at least one specialist 5.

As can be seen from FIG. 2, corresponding solution approaches 27* for this are advantageously stored in the respective data sets 30.

By the automatic determination of a specialists suitable to solve the problem dependent on the data sets 30 selected by the user 4, it is ensured that a user 4 is immediately conveyed to the correct specialist 5, whereby a high user-friendliness is ensured.

In an embodiment not shown in the figures, the control device 2 thereby additionally takes into account information stored in the data storage 1 with regard to the time planning and availability of the specialist 5 and outputs only actually-available specialists 5 to the user 4. If no highly-qualified specialist 5 is available to solve the problem, contact information for contacting an available, less-qualified specialist 5 is automatically output to the user 4 via the user interface 3 by the control device 2.

The decision of whether contact information to contact at least one specialist 5 are output can advantageously be automatically made by the control device 2 in the event that the control device 2, using the combination of data sets 30 input by the user 4, comes to the conclusion that the problem that has occurred in the system has reached a certain minimum level of difficulty.

In the embodiment shown in FIG. 1, the control device 2 is fashioned to automatically provide (via the user interface 3 and the communication device 6) a contact 9 with the at least one specialist 5 suitable to solve a respective problem. This contact 9 can be, for example, a telephone connection or a connection over the Internet.

In order to completely inform the specialist 5 from the outset about the problem that has occurred in the system, using the at least data set 30 or the combination of data sets 30 selected by the user the control device 2 automatically creates a problem context and outputs this to the at least one specialist via the communication device 6. This automatic transfer of the problem context prevents that information already acquired by a user 4 has to be queried again by the specialist 5. Furthermore, the specialist 5 can thus form an image of the existing problem particularly quickly. Since the problem context is automatically created by the control device 2, it uses uniform concepts that are also definitely understandable by the specialist 5, such that misunderstandings between the specialist 5 and the user 4 can be avoided.

Since the (advantageously automatically) created and transferred problem context normally comprises all information necessary for the specialist 5, an unnecessary additional data exchange between the specialist 5 and the user 4 to delimit the problem can be avoided.

The transfer of the problem context to the specialist 5 can thereby, for example, ensue via Internet, as e-mail or as SMS using a mobile telephone.

So that the detection and handling of problems occurring in a system by means of the inventive apparatus A can be continuously improved, it is advantageous to allow, via the user interface 1, an addition of: synonyms 23, 23* for the designation 20 of the problem, and/or solution approaches 27, 27*, and/or information about superordinate or subordinate categories 21, 22; and/or descriptions 24 of the problem, and/or indications 26 of problems possibly connected with the problem, to the data sets 30 stored in the data storage 1 by the user 4 or the specialist 5. An alteration of the data set 30 by a user 4 should normally require the authorization by a specialist 5 in order to ensure that the quality of the detection and handling of problems occurring in a system by means of the inventive apparatus A does not decrease.

The inventive apparatus A can be directly integrated, for example, into a system in which the problems to be remedied occur, such as, for example, a medical apparatus. However, it is also particularly advantageous when the inventive apparatus A is used in connection with a service center in which less-qualified personnel are employed in order to given a customer the feeling of particularly good care. In this case, the user 4 is not the end customer (and therewith the user of the system in which the problems occur) but rather the employee of the service center.

In the following, two typical scenarios are described in which the inventive apparatus A can be used for structured detection and handling of problems occurring in a system.

In a first scenario, the user 4 establishes that an online storage of the system is running in advance. He starts the inventive apparatus 0 for structured detection and handling of problems occurring in a system and selects the designation 20 "Online storage overflow" from the designations 20 shown by the user interface 3 under the main category 21 "Storage" and the sub-category 22 "Online storage". The control device 2 thereupon automatically checks whether a feedback to sub-components and in particular to the online storage is active. If the control device 2 establishes that the online storage is active and the data set with the designation 20 "Online storage overflow" is selected, from this combination it automatically determines the solution approach 27 "insert new storage medium" or "check robotics" and outputs this to the user 4 via the user interface 3.

If the user establishes that in fact no tapes were inserted into the online storage the user inserts these and the problem occurring in the system is remedied. However, if the problem can also not be remedied via insertion of new storage media and via checking of the robotics, the control device 2 outputs the solution approach 27* via the user interface 3, and therewith contact information for contacting the specialist of the field of expertise 23 (online storage) in the form of a specific telephone number and e-mail address.

In the second scenario, a user 4 of the system establishes that images requested in the system cannot be loaded as expected after a few seconds. The user starts the inventive apparatus 0 for structured detection and handling of problems occurring in the system and selects the designation "Images are not loaded" in the output (hierarchically sorted by the user interface 3) of designations 20 of data sets 30. The control device 2 simultaneously, automatically searches via the error handling 7 for specific patterns in the error files and/or check files generated by the system, and thus establishes that a hardware problem exists. As a consequence of the combination thus established of the presence of a hardware problem and the designation "Images are not loaded" selected by the user, the control device 2 automatically determines a suitable solution approach 27, 27* and outputs this to the user 4 via the user interface 3.

In the following, a particularly preferred embodiment of the inventive method for structured detection and handling of problems that have occurred in a system is described under reference to FIG. 5.

A hierarchical sorting of the designations of known problems occurring in a system according to categories ensues in a first step S1, whereby the designations are respectively linked with at least one solution approach to solve the problem.

The designations are output to a user in the following step S2.

A simultaneous selection by the user of a plurality of designations of a plurality of known problems occurring in the system subsequently ensues in step S3.

In the following step S4, a solution approach linked with the respective designation is determined dependent on the respective combination of the designations selected by the user; and the solution approach is output to the user.

Since the determination of the solution approach automatically ensues dependent on the respective combination of the designations selected by the user, it is clear that the user is successively guided to the correct solution. This ensues by the problem of the user always being further delimited dependent on the user input via selection of a designation. A continuously-improving pre-selection of possible considered designations that direct the user to a solution of the current problem thus ensues. In this context it is advantageous when, dependent on the respective user association 29 of the data sets 30, only the data sets 30 that are considered for a respective user are shown to a user.

In step S5 it is checked whether the solution approach comprises an establishment of contact with a specialist assigned with the solution.

If this is not the case, the solution approach is output and the method is terminated.

However, if the solution approach comprises an establishment of contact with a specialist entrusted with the solution of the problem, the specialist suitable for solving the problem is thus automatically determined dependent on a designation or a combination of designations selected by the user.

Contact information for contacting the at least one automatically determined specialist is subsequently automatically output as a solution approach, and in the following step S9 a contact is automatically provided with the at least one specialist suitable for solving the particular problem.

A problem context is subsequently, automatically generated in step S10 using a designation or a combination of designations selected by the user and is automatically output to the at least one specialist in step S11 before the method terminates.

It is clear that the steps S10 and S11 can also advantageously ensue before the steps S7, S8 and S9 or simultaneously with the steps S7, S8 and S9.

According to a further embodiment (not shown in FIG. 5) of the inventive method, an automatic search for specific patterns in error files and/or check files generated by the system and an automatic linking of found patterns with at least one designation of at least one associated problem ensues in parallel with step S1.

Furthermore, it is advantageous for the method also to include the step of the addition of: synonyms for the designation of the respective problem; and/or solution approaches; and/or information about superordinate and/or subordinate categories; and/or descriptions of the respective problem; and indications of problems possibly connected with the respective problem; at an arbitrary point in time to the designations of known problems occurring in the system.

It is particularly advantageous for the inventive method to be implemented in the form of a computer program product which comprises a program code stored on a machine-readable medium that is suitable for execution of the inventive method when it is loaded into the working memory of a computer.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for structured detection and handling of problems that occur in a computerized system, comprising:

a data storage containing a plurality of data sets, each data set concerning a known problem that can occur in a computerized system and each data set comprising at least one solution approach to solve the problem with which this the data set is concerned, and a designation of said problem;

a control device having access to the data storage;

a user interface connected to the control device;

said control device being configured to supply said user interface with a display of the respective designations of the respective problems with which said data sets in said data storage are concerned, and said user interface enabling a simultaneous selection from said display by a user, dependent on the respective designations, of a plurality of said data sets forming a selected combination, and said control device, in response to said selected combination, being configured to automatically determine at least one solution approach to a problem in said computerized system represented by said selected combination, and supplying said at least one suitable solution approach for presentation to said user via said user interface; and said control unit, in said at least one solution approach supplied to said user interface, being configured to include contact information for at least one specialist suitable for responding to said problem.

2. An apparatus as claimed in claim 1 comprising a communication device allowing the user to contact said specialist.

3. An apparatus as claimed in claim 2 wherein said control device is connected to said communication device and automatically generates a problem context, describing said problem, based on the selected combination and supplies said problem context to said specialist via said communication device.

4. An apparatus as claimed in claim 1 comprising an error handling unit configured to automatically search through a plurality of files, selected from the group consisting of error files and check files, created by said computerized system, to identify a pattern, and to automatically store a link to said pattern in at least one of said data sets in said data storage concerning at least one problem that can occur in said computerized system.

5. An apparatus as claimed in claim 1 wherein said user interface presents said respective designations of said data sets hierarchically sorted according to categories.

6. An apparatus as claimed in claim 1 wherein the problem with which at least one of said data sets in said data storage is concerned comprises a plurality of categories, with each category comprising a plurality of sub-categories, and wherein said at least one of said data sets comprises data representing said categories and sub-categories that are presented at said user interface when said at least one of said data sets is supplied to said interface by said control unit.

7. An apparatus as claimed in claim 1 wherein at least one of said data sets in said data storage comprises data representing at least one item selected from the group consisting of a synonym for said designation of the problem with which the data set is concerned, a verbal description of the problem, and an indication of other problems possibly associated with the problem with which the data set is concerned.

8. An apparatus as claimed in claim 1 wherein said user interface allows the user to add, to at least one of said data sets in said data storage, an item selected from the group consisting of a synonym for the designation of the problem with which the data set is concerned, other solution approaches to the problem with which the data set is concerned, information describing categories that are superordinate to the problem with which the data set is concerned, categories that are subordinate to the problem with which the data set is concerned, a verbal description of the problem with which the data set is concerned, and indications of other problems possibly connected with the problem with which the data set is concerned.

9. An apparatus as claimed in claim 8 wherein said user interface permits said addition to said at least one of said data sets only upon input of a recognizable authorization.

10. A method for structured detection and handling of problems that occur in a computerized system, comprising a data storage, a control device and a user interface, said method comprising the steps of:

in said data storage, storing a plurality of data sets, each data set concerning a known problem that can occur in the computerized system and each data set comprising at least one solution approach to solve the problem with which this the data set is concerned, and a designation of said problem;

through said control device, supplying said user interface with a display of the respective designations of the respective problems with which said data sets in said data storage are concerned and, via said user interface, enabling a simultaneous selection by a user, dependent on the respective designations of a plurality of said data sets, to form a selected combination and, in said control device, in response to said selected combination, automatically determining at least one solution approach to a problem in said computerized system represented by said selected combination, and supplying said at least one suitable solution approach for presentation to said user via said user interface; and in said at least one solution approach supplied to said user interface, including contact information for at least one specialist suitable for responding to said problem.

11. A method as claimed in claim 10 comprising providing a communication device allowing the user to contact said specialist.

12. A method as claimed in claim 11 wherein said control device is connected to said communication device, and said method comprising automatically generating a problem context in said control device, describing said problem, based on the selected combination and supplying said problem context to said specialist via said communication device.

13. A method as claimed in claim 10 wherein said computerized system comprises an error handing unit, and said method in said comprising, in said error handling unit, automatically searching through a plurality of files, selected from the group consisting of error files and check files, created by said computerized system, to identify a pattern, and automatically storing a link to said pattern in at least one of said data sets in said data storage concerning at least one problem that can occur in said computerized system.

14. A method as claimed in claim 10 comprising, via said user interface, presenting said respective designations of said data sets hierarchically sorted according to categories.

15. A method as claimed in claim 10 wherein the problem with which at least one of said data sets in said data storage is concerned comprises a plurality of categories, with each category comprising a plurality of sub-categories, and wherein the step of storing said data sets comprises storing, in at least one of said data sets, data representing said categories and sub-categories that are presented at said user interface when said at least one of said data sets is supplied to said interface by said control unit.

16. A method as claimed in claim 10 wherein the step of storing said data sets comprises storing, in at least one of said data sets, data representing at least one item selected from the group consisting of a synonym for said designation of the problem with which the data set is concerned, a verbal description of the problem, and an indication of other problems possibly associated with the problem with which the data set is concerned.

17. A method as claimed in claim 10 comprising allowing a user to add, via said user interface, to at least one of said data sets in said data storage, an item selected from the group consisting of a synonym for the designation of the problem with which the data set is concerned, other solution approaches to the problem with which the data set is concerned, information describing categories that are superordinate to the problem with which the data set is concerned, categories that are subordinate to the problem with which the data set is concerned, a verbal description of the problem with which the data set is concerned, and indications of other problems possibly connected with the problem with which the data set is concerned.

18. A method as claimed in claim 17, comprising permitting said user to said at least one of said data sets only upon input of a recognizable authorization.

19. A storage medium encoded with computer-readable data loadable into a control unit of a computerized system comprising said control unit and a user interface and a data storage containing a plurality of data sets, each data set concerning a known problem that can occur in a computerized system and each data set comprising at least one solution approach to solve the problem with this the data set is concerned, and a designation of said problem, said data of said storage medium causing said control unit to:

supply said user interface with the respective designations of the respective problems with which said data sets in said data storage are concerned, and to enable said user interface to receive a simultaneous selection by a user, dependent on the respective designations of a plurality of said data sets forming a selected combination and to cause said control device, in response to said selected combination, to automatically determine at least one solution approach to a problem in said computerized system represented by said selected combination, and to supply said at least one suitable solution approach for presentation to said user via said user interface; and in said at least one solution approach supplied to said user interface, include contact information for at least one specialist suitable for responding to said problem.

* * * * *